United States Patent [19]

Jacobsson

[11] 4,169,655
[45] Oct. 2, 1979

[54] PROTECTIVE DEVICE FOR PROTECTION AGAINST RADIATION DURING WELDING

[75] Inventor: Jan R. Jacobsson, Täby, Sweden

[73] Assignee: AGA Aktiebolag, Lidingö, Sweden

[21] Appl. No.: 753,627

[22] Filed: Dec. 23, 1976

Related U.S. Application Data

[63] Continuation-in-part of Ser. No. 640,247, Dec. 12, 1975, abandoned, which is a continuation-in-part of Ser. No. 451,165, Mar. 14, 1974, abandoned.

[30] Foreign Application Priority Data

Dec. 23, 1975 [SE] Sweden .................... 7514649
Dec. 23, 1975 [SE] Sweden .................... 7514650

[51] Int. Cl.$^2$ .................... G02B 5/28; G02B 5/23
[52] U.S. Cl. .................... 350/1.7; 350/166; 428/428; 428/433
[58] Field of Search .................... 350/1, 164–166, 350/1.7; 427/160, 165–167; 428/433, 428

[56] References Cited

U.S. PATENT DOCUMENTS

| | | | |
|---|---|---|---|
| 3,042,542 | 7/1962 | Anders | 350/166 |
| 3,269,267 | 8/1966 | Collins | 350/1 |
| 3,499,697 | 3/1970 | Edwards | 350/166 |
| 3,516,720 | 6/1970 | Mauer | 350/1 |
| 3,528,726 | 9/1970 | Austin | 350/166 |
| 3,649,359 | 3/1972 | Apfel et al. | 350/166 |
| 3,679,291 | 7/1972 | Apfel et al. | 350/164 |
| 3,756,692 | 9/1973 | Scott | 350/1 |
| 3,914,516 | 10/1975 | Ritter | 350/164 |
| 4,045,125 | 8/1977 | Farges | 350/166 |
| 4,048,039 | 9/1977 | Daxinger | 350/1 |

FOREIGN PATENT DOCUMENTS

| | | | |
|---|---|---|---|
| 1204232 | 11/1965 | Fed. Rep. of Germany | 252/300 |
| 1234409 | 2/1967 | Fed. Rep. of Germany | 252/300 |
| 2344283 | 3/1974 | Fed. Rep. of Germany | 350/1.7 |
| 366207 | 4/1974 | Sweden | 350/1.7 |
| 1308901 | 3/1973 | United Kingdom | 350/1.7 |

Primary Examiner—Ronald J. Stern
Attorney, Agent, or Firm—Lerner, David, Littenberg & Samuel

[57] ABSTRACT

A protective device is disclosed which is useful in protecting an operator against radiation emitted during welding. The protective device, which is employed in the presence of a surrounding light source, includes an interference filter which has a spectrally selective portion with bands for one or more of the ranges of wavelengths present in the emission spectrum of the surrounding light source and a radiation absorbing portion which attenuates the radiation to a value harmless to the eye without interfering with the spectrally selective portion of the interference filter.

24 Claims, 17 Drawing Figures

PROTECTIVE DEVICE FOR PROTECTION AGAINST RADIATION DURING WELDING

CROSS REFERENCE

This is a continuation-in-part application of my prior application, Ser. No. 640,247, filed Dec. 12, 1975 and entitled PROTECTIVE GLASS FOR PROTECTION AGAINST RADIATION DURING WELDING which is co-pending herewith and now abandoned, which in turn is a continuation-in-part application of my prior application, Ser. No. 451,165, filed Mar. 14, 1974 and entitled PROTECTIVE GLASS FOR PROTECTION AGAINST RADIATION DURING WELDING which was co-pending therewith but is now abandoned.

FIELD OF THE INVENTION

The present invention relates to a protective device which includes an interference filter, for protecting a person against radiation during welding.

BACKGROUND OF THE INVENTION

It is well known that when welding work is being conducted, intensive radiation is emitted from a welding arc as well as from the melting zone of the materials being worked on. Such radiation is of an intensity which is harmful to the human eye. At present, in order to protect the operator from this harmful radiation, protective goggles or a protective shield are used which comprise a central region of spectrally absorbing glass which filters out much of the radiation. Moreover, these glasses have the effect of attenuating the intensity of the radiation to values which are harmless to the eye. Unfortunately, these glasses greatly reduce the visibility of the surroundings to the operator so that before the arc is lit and welding commences, the operator or welder can see very litte. As a result, the ability of orientation of the welder will be unsatisfactory and he will therefore have to remove or push aside the shield or the goggles in order to place the welding electrode in its correct position at the start of welding.

To improve conditions for the welder, it has been suggested to use an interference filter instead of the aforementioned spectrally absorbing glass. The filter would have pass bands for one or more ranges of wavelengths in the visible part of the spectrum of the arc, the intensity in these ranges of wavelengths having values which are harmless to the eye. The remaining wavelengths in the spectrum are extinguished by the filter. However, the use of an interference filter of these properties also has the disadvantage that the visibility of the surroundings is unsatisfactory.

One method to achieve visibility of the surroundings, even when the welding arc is not lit, consists in the use of a special light source in the surrounding space. The spectrum of the light source will be restricted to one or more narrow ranges of wavelengths. Sodium lamps are an example of such a light source. The interference filter which is used in the protective glass will then have pass bands for the range or ranges of wavelengths emitted by the light source. With the help of such a light source in the surrounding space visibility of the surroundings is obtained both before the arc has been lit and while it is lit.

This arrangement, however, has a substantial disadvantage in that the radiation from that part of the spectrum of the arc which lies outside the pass band of the filter will be strongly reflected from the surface of the interference filter and consequently disturb the surroundings. This mirror-like strong reflection from the filter also has the disadvantage that, when the welding arc is not lit, the welder will see his mirror image in the protective glass instead of the object he wants to observe through the protective glass.

Mirror-like qualities of the interference filter can be overcome by putting optically thick layers of absorbing material on both sides of the interference filter. The absorbing material on the front side would prevent the mirror image from disturbing the surrounding areas while the absorbing material on the other side would prevent the operator from seeing his reflection. Unfortunately, the placing of optically thick absorbing material on both sides of the interference filter would result in a device which was bulky and therefore not suited as lenses for a welding mask and further would be too expensive to manufacture commercially.

Since interference filters operate upon principles involving the thickness of the layers thereof, the adding of thin absorbing layers to the front and back of the interference filter would be expected to change the spectral characteristics thereof producing a new interference filter which would still have the mirror-like characteristics.

SUMMARY OF THE INVENTION

To overcome the problems of the prior art, a protective device for protection against radiation is provided which includes a filter having a spectrally selective portion which may comprise an all dielectric interference filter or a metal interference filter, having pass bands for one or more of the ranges of wavelengths of light which are present in the emission spectrum of the light source. On both sides of the spectrally selective portion is an absorbing portion. The absorbing portions may be made of single or multiple layers. If made of a single layer, that layer must be of an absorbing material. If made of multiple layers, at least one of the layers must be of an absorbing material.

The device further includes surrounding media which form optically thick layers which surround the filter. The absorbing portions of the filter are adapted so that the reflectance between the filter and the surrounding media assumes neutrally low values and the spectral function of the selective portion of the filter remains largely unaffected by the surrounding layers of the absorbing portions.

In a preferred embodiment of this invention, the absorbing portions are further adapted so that the reflectance between the absorbing portions and the spectrally selective portion of the interference filter assumes neutrally low values. In this way the absorbing portions attenuate the light in the pass band (as well as in the bands not passed) and further minimize reflectance at the two interfaces thereof rendering the absorbing portions unable to affect the spectral characteristics of the spectrally selective portion of the interference filter and further absorbing mirror-like reflections from the spectrally selective portion of the interference filter.

In accordance with a further aspect of this invention, the absorbing portions include layers of absorbing material and layers of non-absorbing material. The absorbing portion is constructed by depositing the absorbing and non-absorbing material in layers of varying amounts. At the boundaries of the absorbing portions, the layers consist essentially of the non-absorbing material.

In accordance with yet another aspect of the invention, at least one of the surrounding media is comprised of a solid material, which may be absorbing or non-absorbing. For example, the surrounding media may be glass in the form of a plate with a plane or curved surface.

In accordance with still another aspect of this invention, a light sensitive substrate is provided, the transmission of which is reduced upon increased illumination. This affords a degree of protection to the user from the harmful effects of large fluctuation of light intensity.

BRIEF DESCRIPTION OF THE DRAWINGS

The invention will be further described in more detail in conjunction with the accompanying drawings wherein.

DETAILED DESCRIPTION

Figure 1:
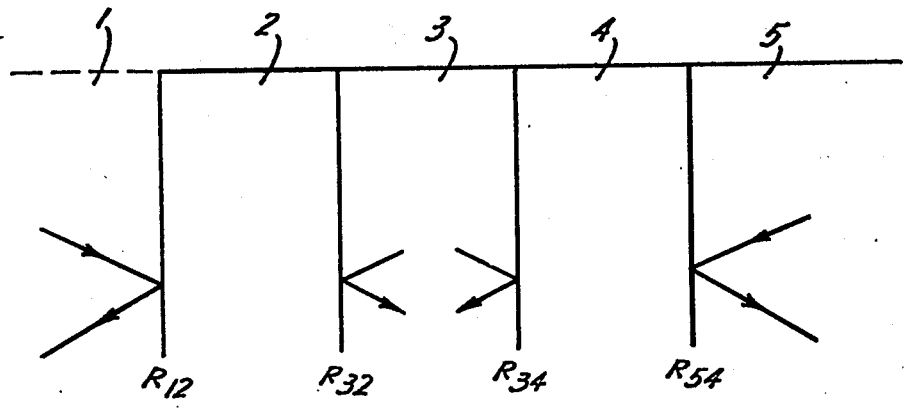
FIG. 1 schematically illustrates the structure of a protective device constructed in accordance with the principles of this invention.

FIG. 1 shows the structure in principle of a device constructed in accordance with the principles of this invention. The device comprises an interference filter made of portions 2, 3 and 4. The portion 3 is spectrally selective and may be comprised of a wholly dielectric interference filter or a metal interference filter of a type known per se, such as, for example, of the multiple cavity type, a Fabry-Perot filter or combinations of longpass and shortpass filters. The spectrally selective part 3 of the device generates one or more pass bands within which the light source in the surrounding space has its main emission.

The portions 2 and 4 are layers of approximately one micron in thickness which are employed to attenuate the light passed by the pass band of the spectrally selective part 3 and absorb the radiation normally reflected by the spectrally selective part 3 so that the filter does not appear to be a mirror and yet the layers 2 and 4 do not interfere with the proper operation of the spectrally selective part 3. It should be appreciated that when putting a thin absorbing material such as layers 2 and 4 onto an interference filter such as spectrally selective part 3 the new thin layers become part of the interference structure and change the overall spectral characteristics. This phenomena occurs because new reflections occur at the new interfaces which now provide reflective light which interacts with the other reflected light generated in the other layers of the interference filter.

Figure 2:
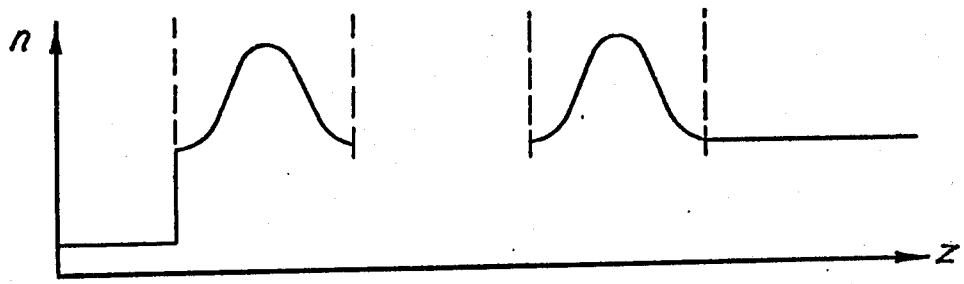
FIG. 2 depicts a first illustrative refractive index of a portion of the device shown in FIG. 1.

To overcome this problem the coefficients of reflection R 12 and R 54 between the portions 2 and 4 and their respective surrounding media (parts 1 and 5) is kept to a low value, preferably between 0 and 10%. In this way only a small percentage of the light incident upon these surfaces will be reflected back into the filter. Unfortunately, in order to keep the coefficients of reflection low, it is necessary to have a non-absorbing material at the interface. Therefore, in accordance with the teachings of this invention, the refractive index in the layers 2 and 4 are made to vary from the interface with the surrounding media 1 and 5 from a relatively low value to a relatively high value towards the center thereof. In a preferred embodiment of this invention, the reflective index is made to further vary towards a low value at the interface between portions 2 and 4 and the spectrally selective portion 3. FIG. 2 shows a plot of the refractive index n of the device shown in FIG. 1 as a function of the distance z across the cross-section thereof.

By constructing the portions 2 and 4 as described above, several related things occur. Firstly, by keeping the reflection coefficient low at the interface of the surrounding media 1 and 5 and the portions 2 and 4, only a small reflection is seen by a person external to the device. Further, light reflected from the interface between the portions 2 and 4 and the spectrally selective portion 3 will have only a small portion thereof reflected back when it reaches the interface between the surrounding media 1 and 5 and the portion 2 and 4.

In this way the interference phenomena normally occurring in interference filters is attenuated. Further, by having absorbing material in portions 2 and 4, the light reflected from the interfaces of portions 2 and 4 and the spectrally selective portion 3 will be attenuated as it travels therethrough. By further having the reflection coefficient at the interface of the portion 2 and 4 and the spectrally selective portion 3 low, only a small amount of light will be reflected therefrom in the first instance. Therefore, it is seen that by the construction of the portions 2 and 4 as set forth above, light passing through the device from left to right in FIG. 1 will be attenuated as it passes through the portion 2 and only a small portion thereof will be reflected at the interface of the portion 2 and the spectrally selective portion 3. This light will be further attenuated as it passes back through the portion 2 and only a small portion of the light which has been reflected back through the portion 2 will be reflected at the interface of portion 2 and the surrounding media 1. As a result, the thin layer 2 does not interfere with the spectral characteristics of the spectrally selective portion 3. The portion 4 operates in the same fashion. The portions 2 and 4 serve the further function that light rejected by the spectrally selective portion 3 which normally gives the mirror look to an interference filter will be absorbed in passing outwardly through either the portions 2 and 4. In this way, a complex interaction has been developed so that an interference filter comprising the layers 2, 3 and 4 can be constructed having a spectrally selective portion 3 and yet not having the mirror appearance heretofore characteristic of interference filters.

Figure 3:
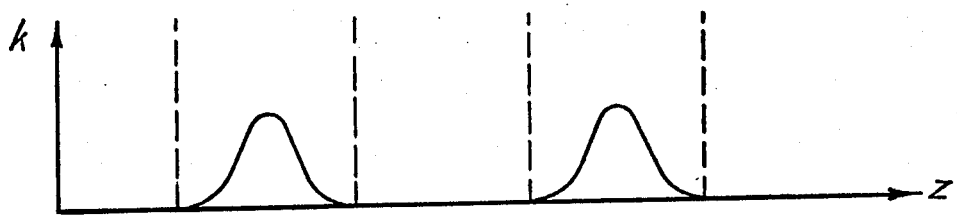
FIG. 3 depicts a first illustrative absorption coefficient as a function of the coordinate perpendicular to the filter surface of a device structure as shown in FIG. 1.

Layers 2 and 4 may be constructed in either one of two ways. In the first way, the layers are non-homogeneous and contain at least one absorbing and one non-absorbing material. The absorbing material may be, for example, a metal oxide or a metal such as chromium or chromium oxide, while the non-absorbing material may be silicon dioxide. The portions 2 and 4 may be manufactured by vacuum deposition with the concentration of the absorbing and non-absorbing materials varying over the cross section thereof. FIG. 3 shows the absorption coefficient k in the cross section of the portion 2 and 4. It is seen that at the interfaces with the surrounding media 1 and 5 and the spectrally selective portion 3 the non-absorbing material dominates while in the central portion, the absorbing material has a higher concentration.

It is also seen that the concentration varies smoothly so that the refractive index will vary smoothly across the cross section of the portions 2 and 4 so that the change in refractive index within distances of the relative order of magnitude of the wavelength of light in the medium will be sufficiently small in relation to the refractive index in portion 1 so that a minimum reflected wave is generated therein.

Figure 4:
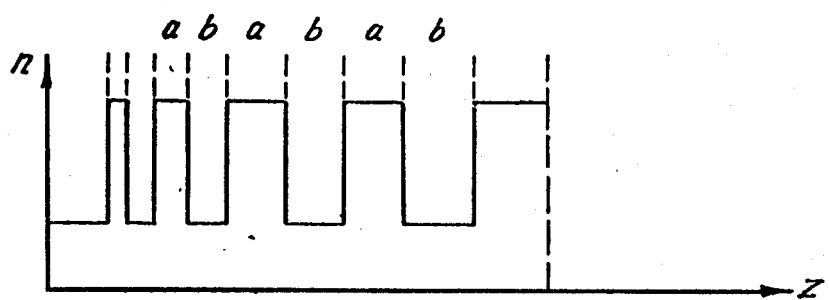
FIG. 4 depicts the refractive index of a generalized second embodiment of the device structure of the invention.
Figure 5:
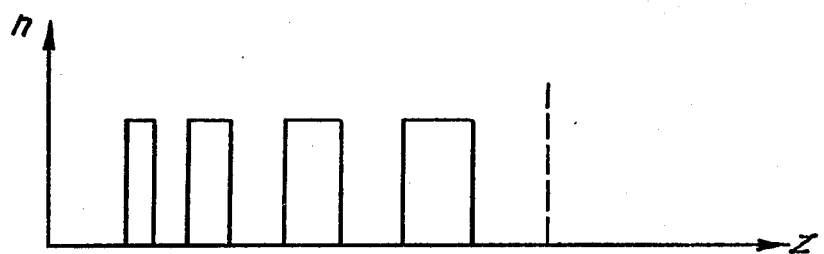
FIG. 5 illustrates the absorption coefficient of the generalized second embodiment of the device structure of the invention.

The second way of constructing the portions 2 and 4 is to provide discreet very thin layers which interact in a way to give the same result as described above. FIG. 4 shows generalized absorption coefficient k of such a structure where a designates a dielectric layer and b designates a metal layer. FIG. 5 shows the refractive index n produced thereby. This refractive index produces the result on the light passing therethrough as does the refractive index shown in FIG. 2.

The following examples 3-7 show illustrative constructions for parts 2, 3 and 4 of the device shown in FIG. 1 which provide the desired characteristics when using a light source in the surroundings having an emission of wavelength 589 nanometers, sodium lamps having an emission at 590±2 nanometers.

EXAMPLE 3 FOR THE WAVELENGTH λ=589 nm

The composition and thickness of the layers in the multiple layers

|  | Layer No. | Material | Thickness (nm) |
|---|---|---|---|
| part 2 | 1 | SiO$_2$ | 270 |
|  | 2 | Cr | 6 |
|  | 3 | SiO$_2$ | 270 |
|  | 4 | Cr | 6 |
|  | 5 | SiO$_2$ | 270 |
|  | 6 | Cr | 6 |
|  | 7 | SiO$_2$ | 270 |
| part 3 | 8 | Ag | 50 |
|  | 9 | MgF$_2$ | 850 |
|  | 10 | Ag | 50 |
| part 4 | 11 | SiO$_2$ | 270 |
|  | 12 | Cr | 6 |
|  | 13 | SiO$_2$ | 270 |
|  | 14 | Cr | 6 |
|  | 15 | SiO$_2$ | 270 |
|  | 16 | Cr | 6 |

-continued

| Layer No. | Material | Thickness (nm) |
|---|---|---|
| 17 | SiO$_2$ | 270 |

Example 3 comprises an interference filter in combination with a light source having strong emission, mainly around 589 nm, as for instance a sodium lamp or a high pressure mercury lamp, said filter comprising parts 2, 3 and 4 in accordance with FIG. 1. As is apparent from the table, part 2 and part 4 each comprise seven layers, the first layer being made of a film of quartz (SiO$_2$) having a thickness of 270 nanometers, the second layer being made of a film of chromium having a thickness of 6 nanometers, the third, fifth and seventh layers being made of a film of quartz having a thickness of 270 nanometers and the fourth and sixth layers being made of a film of chromium having a thickness of 6 nanometers. Part 3 consists of three layers, the first and third ones being made of a thin film of silver having the thickness of 50 nanometers and the second one being made of a thin film of magnesium fluoride having a thickness of 850 nanometers. It has been found that the use of chromium as the absorbing material in parts 2 and 4 is highly advantageous. The optical properties of chromium as an absorber combined with its strength provide decided advantages over other materials. In addition, chromium adheres very well to quartz.

Figure 6:
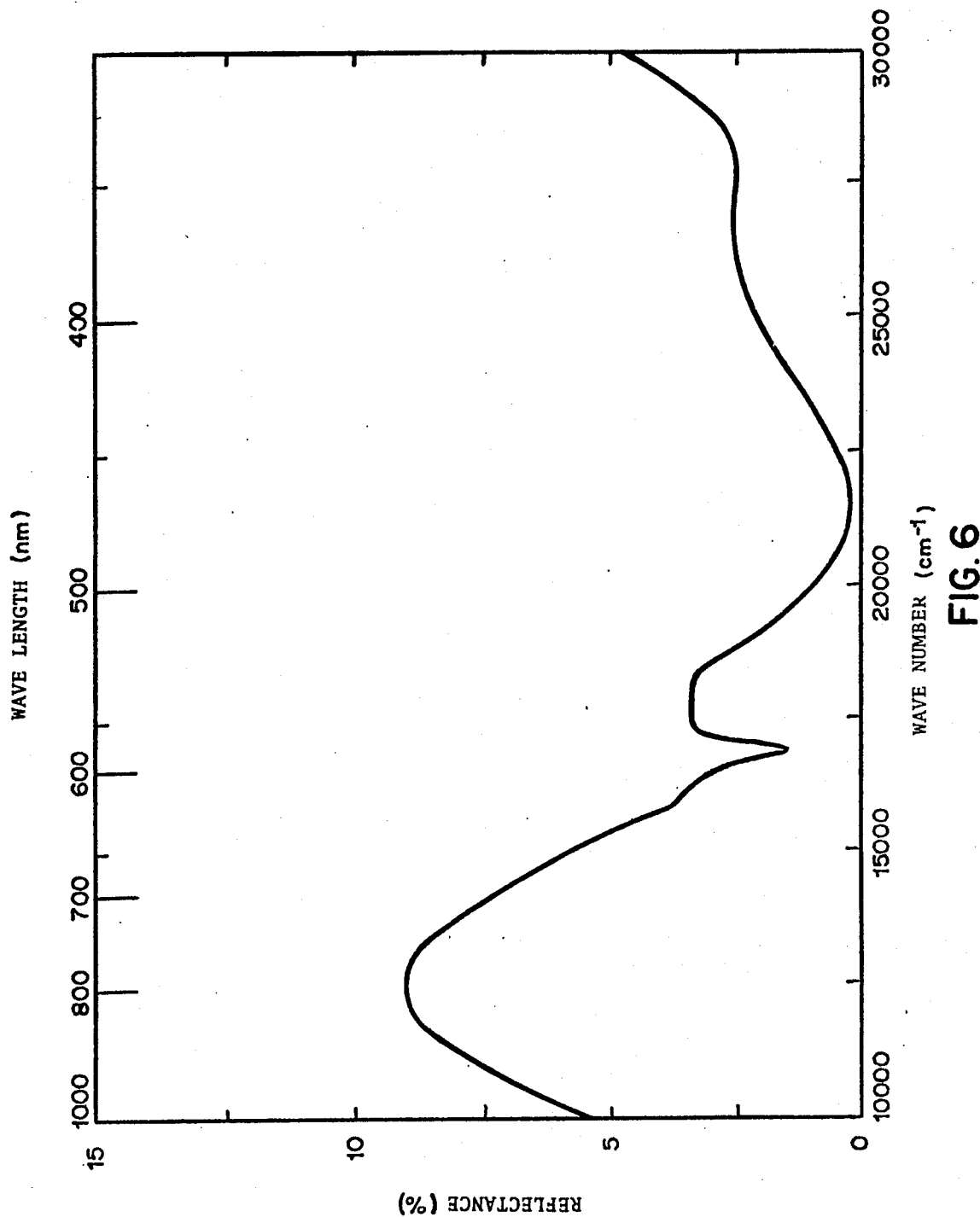
FIG. 6 illustrates the reflectance.
Figure 7:
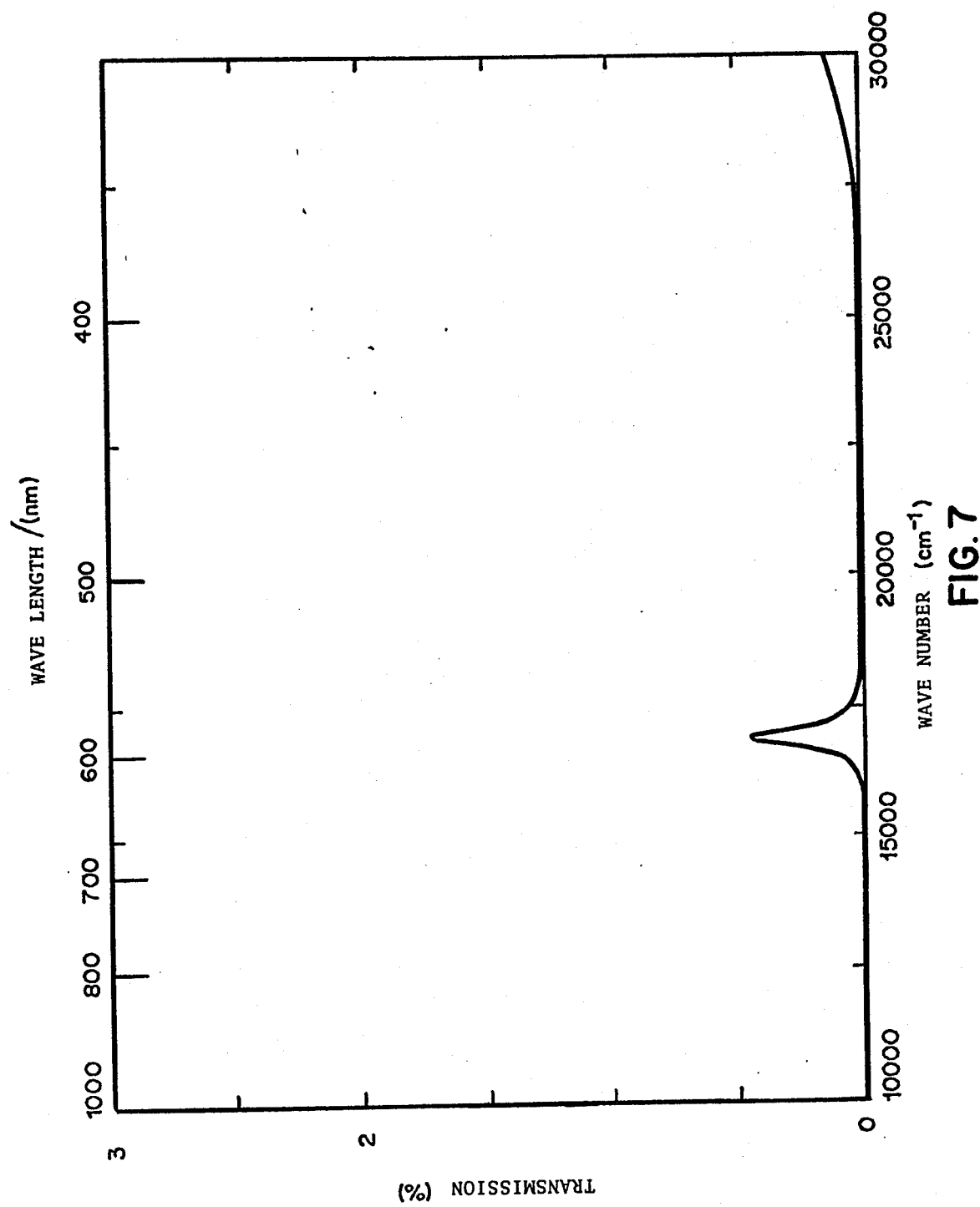
FIG. 7 the transmission of a device according to a specific third embodiment.

FIG. 6 illustrates the reflectance and FIG. 7 the transmission of the filter according to example 3 as a function of the wavelengths in nanometers.

EXAMPLE 4 FOR THE WAVELENGTH λ=589 nm

The composition and thickness of the layers in the multiple layers

|  | Layer No. | Material | Thickness (nm) |
|---|---|---|---|
| part 2 | 1 | Al$_2$O$_3$ | 227 |
|  | 2 | Cr | 6 |
|  | 3 | Al$_2$O$_3$ | 76 |
|  | 4 | Cr | 14 |
|  | 5 | Al$_2$O$_3$ | 76 |
|  | 6 | Cr | 6 |
|  | 7 | Al$_2$O$_3$ | 227 |
| part 3 | 8 | Ag | 33 |
|  | 9 | Al$_2$O$_3$ | 306 |
|  | 10 | Ag | 77 |
|  | 11 | Al$_2$O$_3$ | 841 |
|  | 12 | Ag | 33 |
| part 4 | 13 | Al$_2$O$_3$ | 227 |
|  | 14 | Cr | 6 |
|  | 15 | Al$_2$O$_3$ | 76 |
|  | 16 | Cr | 14 |
|  | 17 | Al$_2$O$_3$ | 76 |
|  | 18 | Cr | 6 |
|  | 19 | Al$_2$O$_3$ | 227 |

Example 4 comprises an interference filter in combination with a light source with emissionn at 589 nm, said filter comprising parts 2, 3 and 4 in accordance with FIG. 1. As is apparent from the table, parts 2 and 4 comprise each seven layers, the first and seventh ones being made of a film of Al$_2$O$_3$ having a thickness of 227 nm, the second and sixth of a film of chromium having a thickness of 6 nm, the third and fifth of a film of Al$_2$O$_3$ having a thickness of 76 nm and the fourth and middle layer being made of a film of chromium having a thickness of 14 nm.

Part 3 consists of five layers, the first and fifth ones consisting of silver having a thickness of 33 nm, the second of a film of Al₂O₃ having a thickness of 306 nm, the third of a film of silver having a thickness of 77 nm and the fourth of a film of Al₂O₃ having a thickness of 841 nm.

Figure 8:
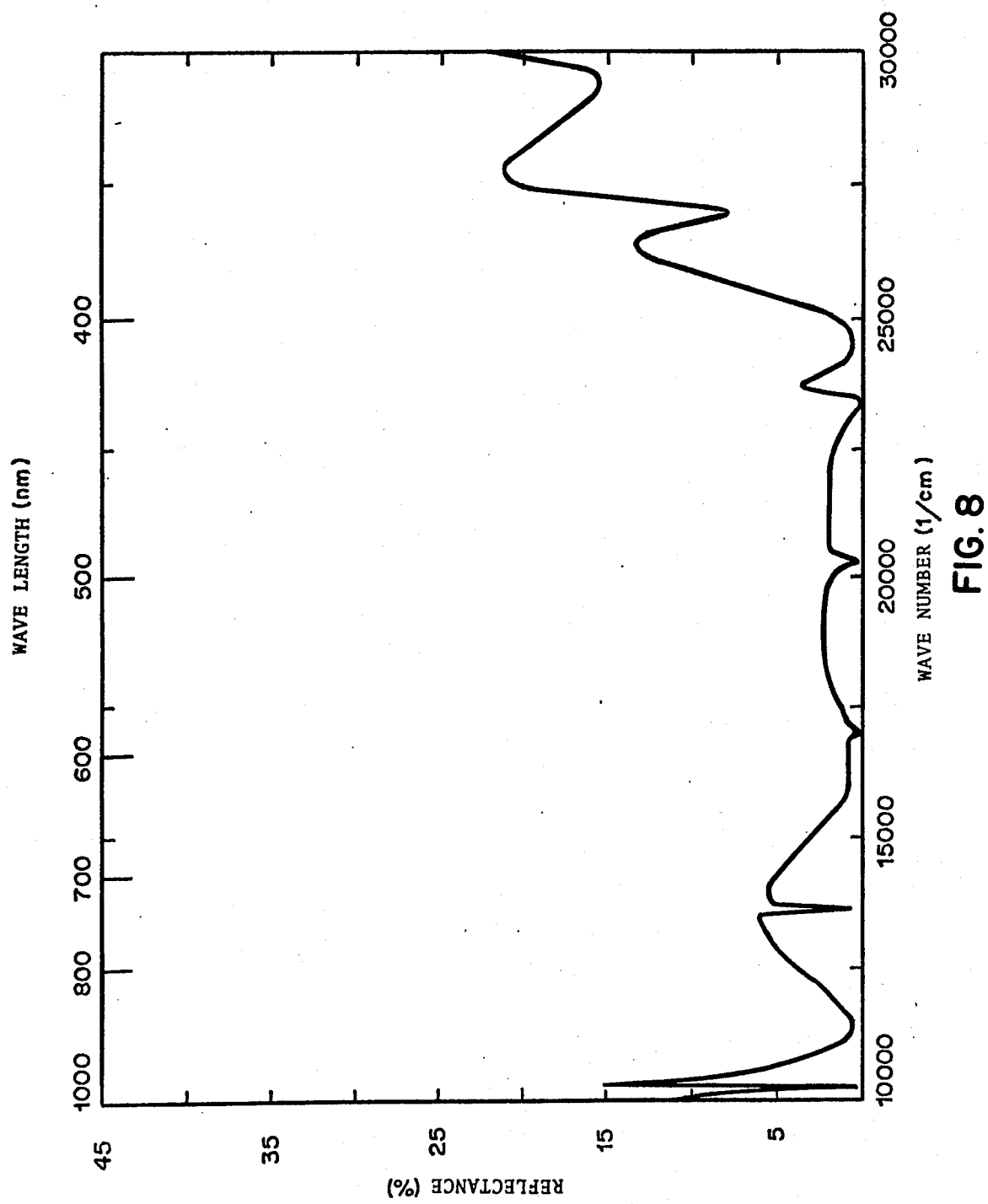
FIG. 8 illustrates the reflectance.
Figure 9:
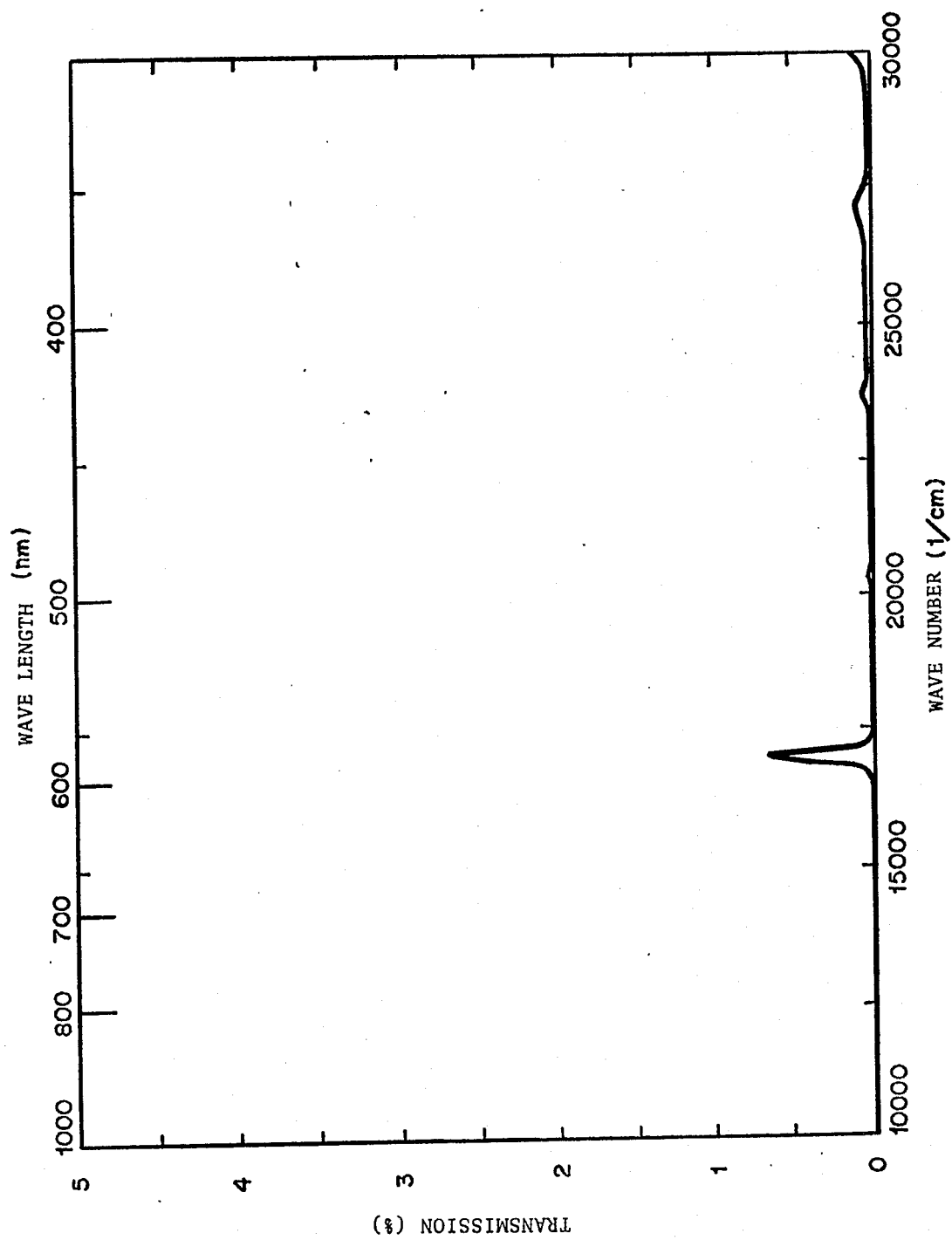
FIG. 9 the transmission of a device according to a specific fourth embodiment.

FIG. 8 shows the reflectance and FIG. 9 the transmission of the device filter according to example 4 as a function of the wavelength in nanometers.

EXAMPLE 5 FOR THE WAVELENGTH λ=589 nm

The composition and thickness of the layers in the multiple layers

| | Layer No. | Material | Thickness (nm) |
|---|---|---|---|
| part 2 | 1 | Al₂O₃ | 227 |
| | 2 | Cr | 6 |
| | 3 | Al₂O₃ | 76 |
| | 4 | Cr | 7 |
| | 5 | Al₂O₃ | 76 |
| | 6 | Cr | 7 |
| | 7 | Al₂O₃ | 76 |
| | 8 | Cr | 6 |
| | 9 | Al₂O₃ | 227 |
| part 3 | 10 | Ag | 33 |
| | 11 | Al₂O₃ | 306 |
| | 12 | Ag | 77 |
| | 13 | Al₂O₃ | 841 |
| | 14 | Ag | 33 |
| part 4 | 15 | Al₂O₃ | 227 |
| | 16 | Cr | 6 |
| | 17 | Al₂O₃ | 76 |
| | 18 | Cr | 7 |
| | 19 | Al₂O₃ | 76 |
| | 20 | Cr | 7 |
| | 21 | Al₂O₃ | 76 |
| | 22 | Cr | 6 |
| | 23 | Al₂O₃ | 227 |

In analogy with the above embodiments the example 5 shown above illustrates an interference filter in combination with a light source with emission at 589 nm, said filter comprising parts 2, 3 and 4 according to FIG. 1. As is evident from the table, parts 2 and 4 each comprise nine layers and part 3 five layers. Example 5 differes from example 4 in that in parts 2 and 4 the middle layer 4 has been exchanged for three layers, the outer layers of which are made of a film of chromium having a thickness of 7 nm and the intermediate layer being made of a film of Al₂O₃ having a thickness of 76 nm.

Figure 10:
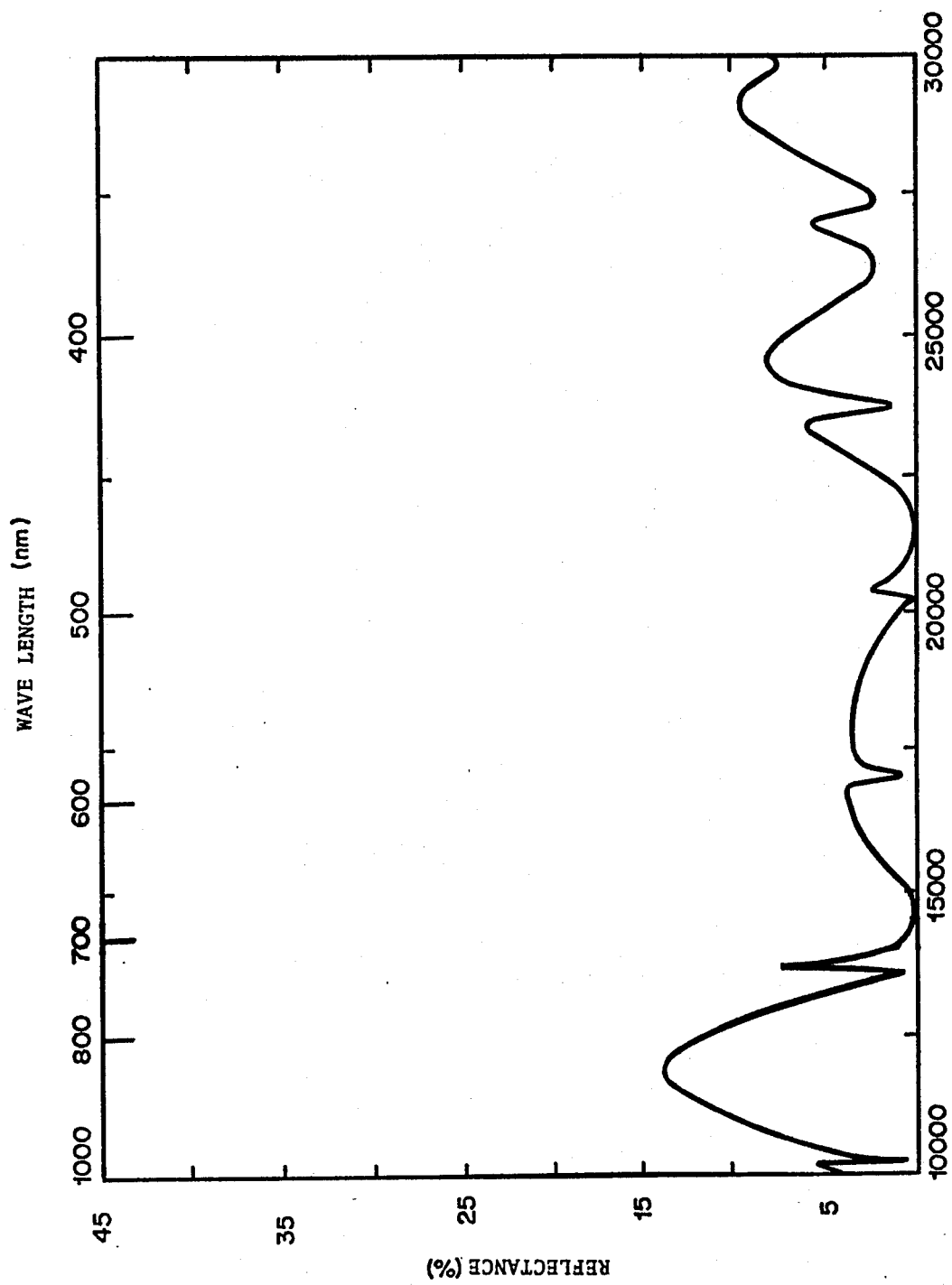
FIG. 10 illustrates the reflectance.
Figure 11:
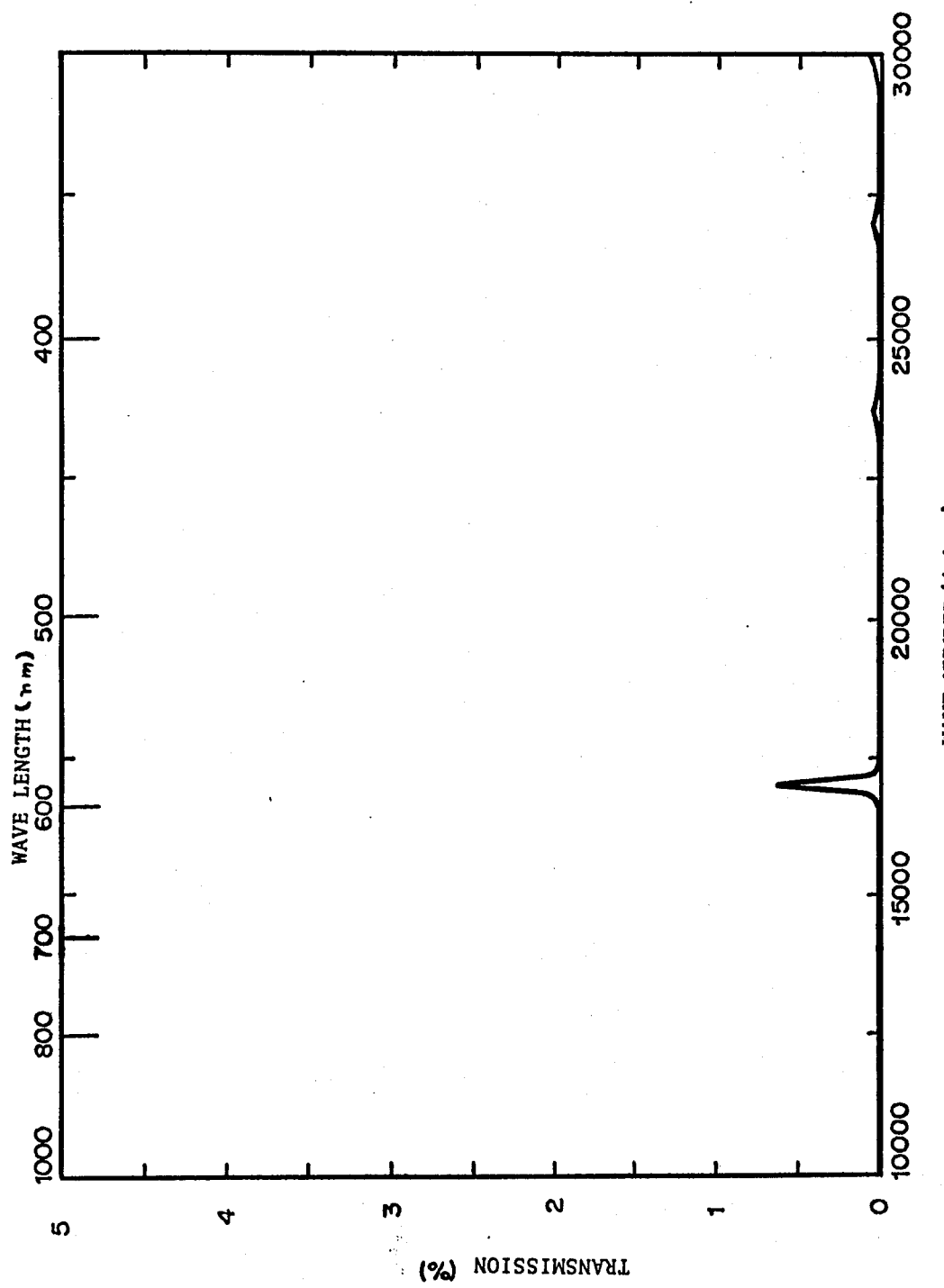
FIG. 11 the transmission of a device according to a specific fifth embodiment.

FIG. 10 illustrates the reflectance and FIG. 11 the transmission of the filter according to example 5.

EXAMPLE 6 FOR THE WAVELENGTH =589 nm

The composition and the thickness of the surrounding multilayers

| | Layer No. | Material | Thickness (nm) |
|---|---|---|---|
| part 2 | 1 | n = 1.35 | 277 |
| | 2 | Cr | 7 |
| | 3 | n = 1.35 | 93 |
| | 4 | Cr | 15 |
| | 5 | n = 1.35 | 93 |
| part 3 | 6 | Ag | 33 |
| | 7 | n = 1.35 | 385 |
| | 8 | Ag | 77 |
| | 9 | n = 1.35 | 604 |
| | 10 | Ag | 33 |
| part 4 | 11 | n = 1.35 | 93 |
| | 12 | Cr | 15 |
| | 13 | n = 1.35 | 93 |

-continued

| Layer No. | Material | Thickness (nm) |
|---|---|---|
| 14 | Cr | 7 |
| 15 | n = 1.35 | 277 |

Example 6 comprises an interference filter in combination with a light source with emission at 589 nm, said filter having parts 2, 3 and 4 in accordance with FIG. 1. As is apparent from the table, parts 2 and 4 are mirror images of each other and comprise five layers each. The dielectric layers are made of a material with a refractive index n=1.35 and examples of such materials are MgF₂, Na₃AlF₆. The first, outer layer is a dielectric film having a thickness of 277 nm, the second layer is a film of Cr having a thickness of 7 nm, the third and the fifth layers are dielectric films having a thickness of 93 nm and the fourth layer is a film of Cr having a thickness of 15 nm.

Part 3 consists of five layers, the first and the fifth ones consisting of silver having a thickness of 33 nm. The third one is also of silver but has a thickness of 77 nm. The second and fourth layers are dielectric films, of which the second has a thickness of 385 nm and the fourth has a thickness of 604 nm.

Figure 12:
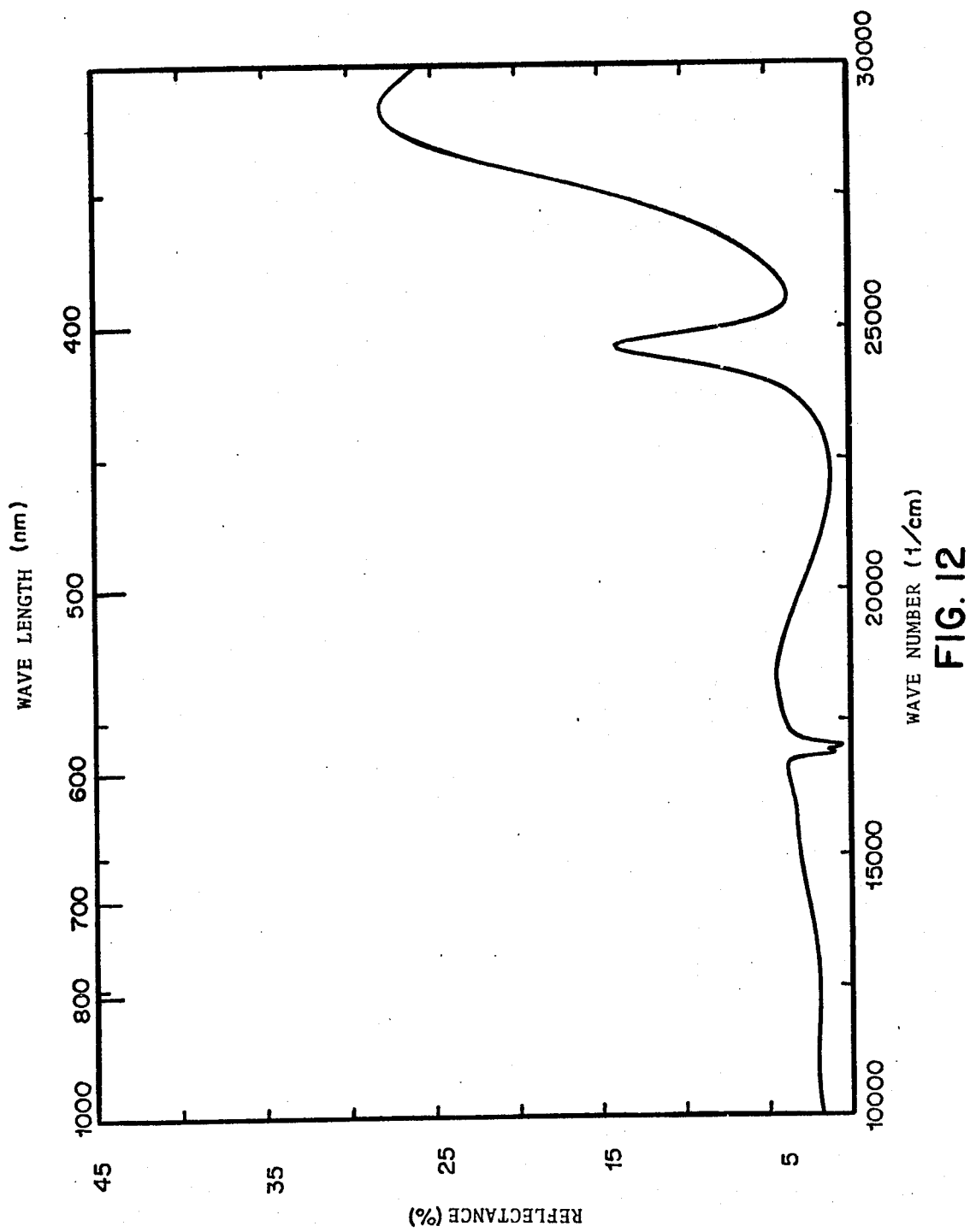
FIG. 12 illustrates the reflectance.
Figure 13:
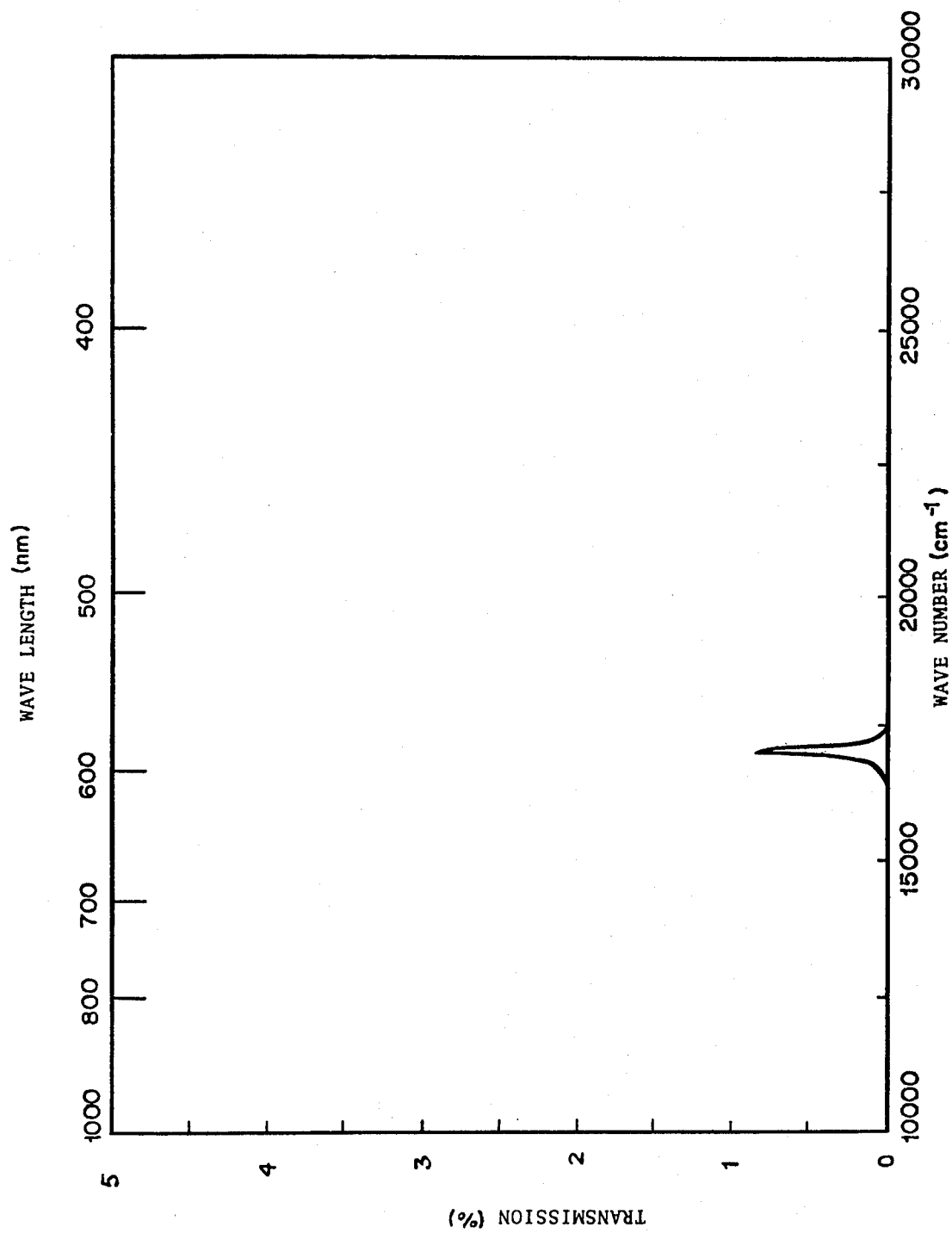
FIG. 13 the transmission of a device according to a specific sixth embodiment.

FIG. 12 shows the reflectance and FIG. 13 the transmission of the filter according to example 6 as a function of the wavelength in nanometers.

Figure 14:
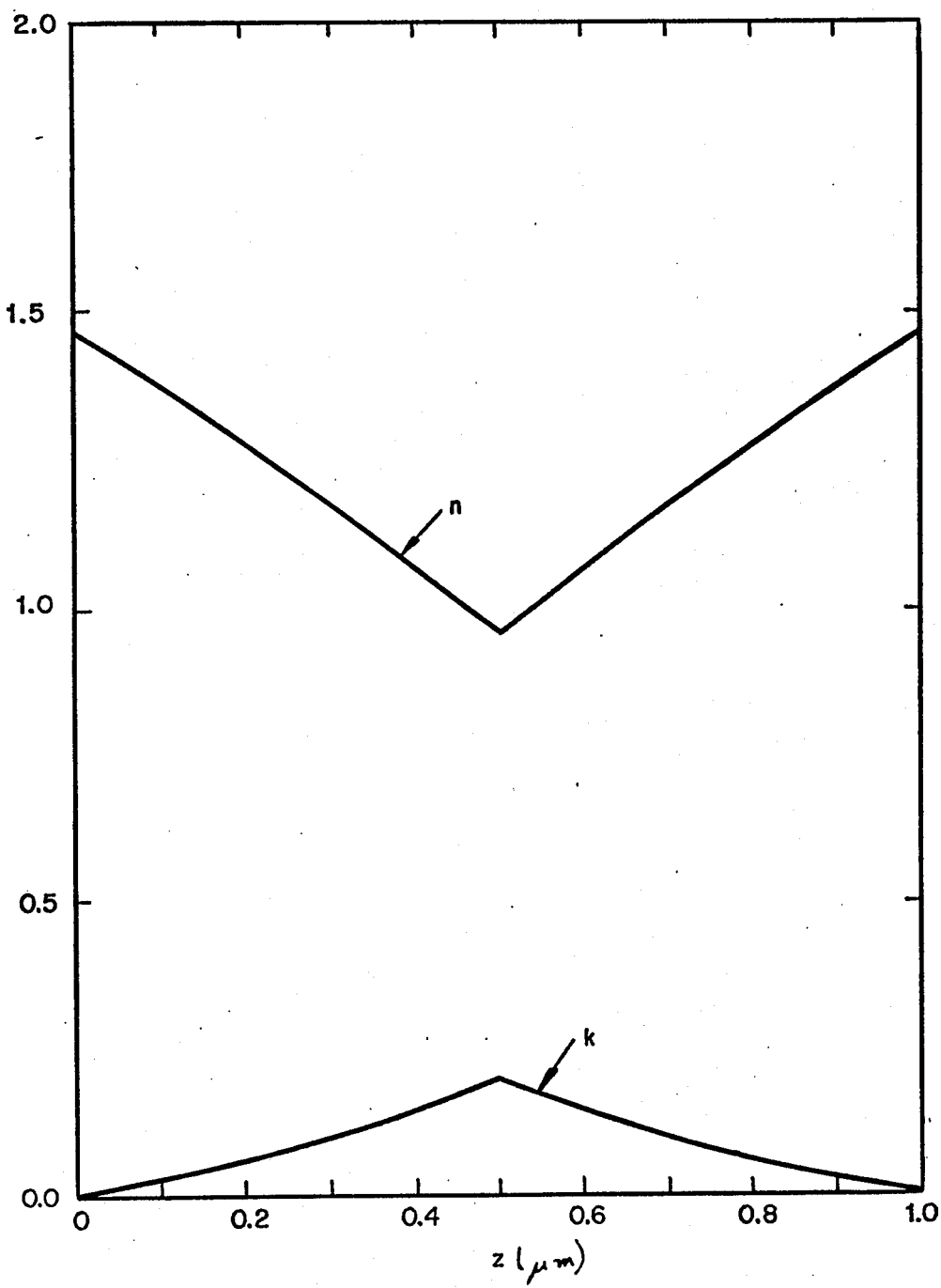
FIG. 14 illustrates the variation of n and k in accordance with a specific seventh embodiment.
Figure 15:
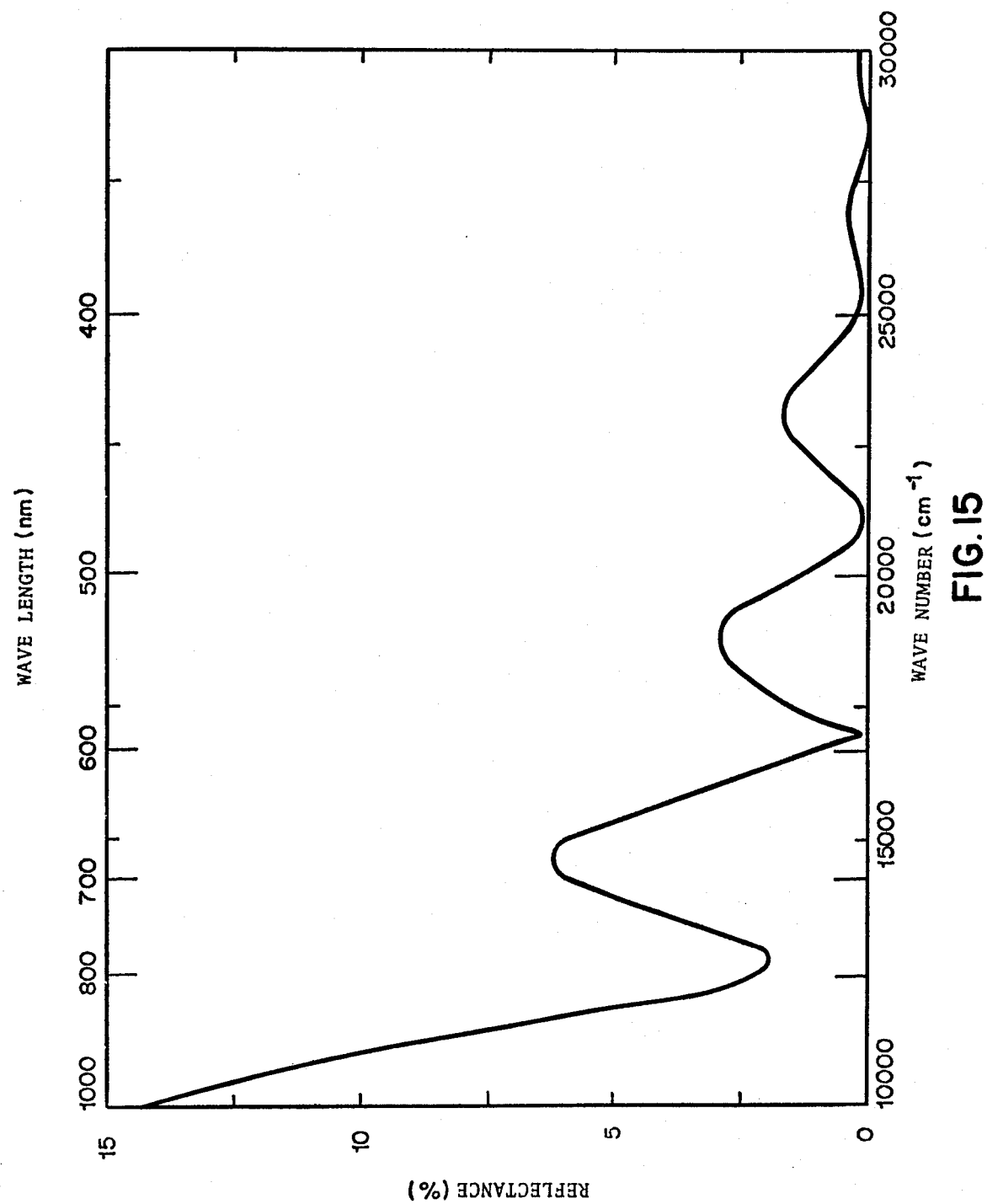
FIG. 15 illustrates the reflectance, and FIG. 16 the transmission of a device according to the specific seventh amendment.
Figure 16:
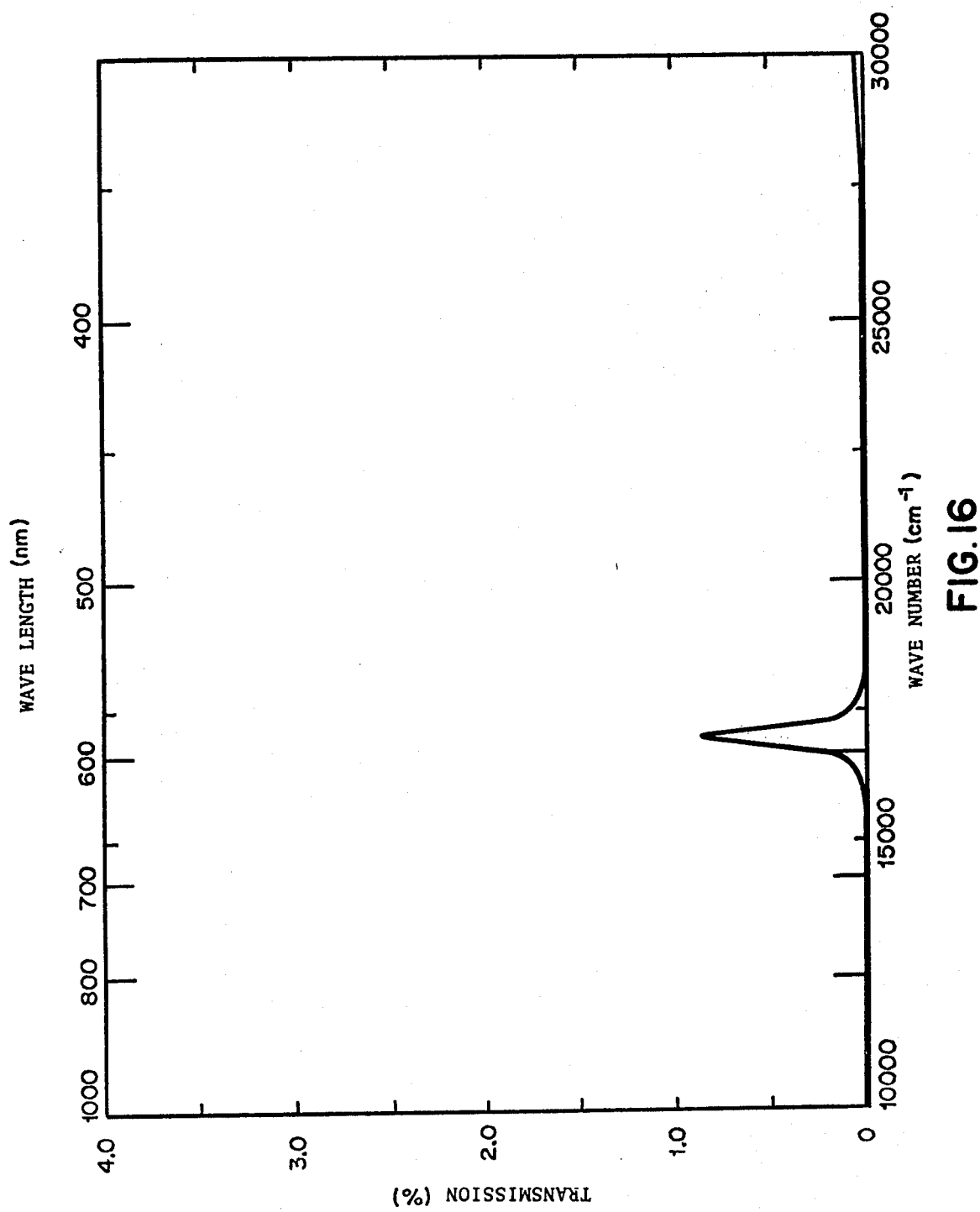

FIG. 14 to 16 illustrate a seventh embodiment. FIG. 14 illustrates the refractive index n and the absorption coefficient k as a function a depth z from the filter surface of parts 2 and 4 in FIG. 1. As is apparent from this figure, parts 2 and 4 have an integrated optical thickness of about 1 μm and are built up symmetrically around their centers. n from each end surface to the middle of the layers then varies from essentially n=1.46 to essentially n=0.95 and k varies from essentially K=0 to essentially k=0.2.

In this seventh embodiment part 3 consists of three layers, the first and third of which being made of a thin film of silver having a thickness of 50 nm and the second of a thin film of magnesium fluoride having a thickness of 690 nm. Parts 2 and 4 each consist of a mixture of aluminum and quartz which is non-uniform in the direction of the normals to the surfaces of the layer.

FIG. 15 shows the reflectance and FIG. 16 the transmission as a function of the wavelength in nm for the seventh embodiment.

The layers in all abovementioned four embodiments may be produced by vacuum deposition. The embodiments of the filter are particularly suitable for sodium discharge lamps with emission at about 589 nm. The construction may be modified in order that the filter can be used also at other wavelengths, for instance for the emission line of the mercury discharge lamp at 546 nm. When adapted to a wavelength other than 589 nm, for which said filters in the abovementioned embodiments are calculated, said filters are modified according to well known optical principles so that the thickness of all provided dielectrical layers are changed according to the formula $h = h' (n'/n)(\lambda/\lambda')$, where h is the thickness of the layer referred to in the modified filter, h' is the thickness of the layer referred to in the above embodiments, n' is the refractive index of the provided dielectric at a wavelength of 589 nm, n is the refractive index at the wanted wavelength, λ is the wanted wavelength and λ' is the wavelength 589 nm. The optical path length is thereby kept constant in the provided partial layer by the transformation.

When dimensioning the above embodiments of the filter according to the invention one has strived to obtain a reflectance as low and even as possible for the whole wavelength region, which is apparent from FIGS. 6, 8, 10, 12 and 15 in which the average reflectance is below 5% and the maximum reflectance within a wavelength region sensitive to the eye is not above 15%.

By means of the filter shape, described above, one has thus obtained a filter which transmits light only within the region or regions of the light source, which suppress the intensity of the light from the welding arc to a value, harmless for the eye, and which does not cause any inconvenient, disturbing, or harmful reflections to the surroundings. Filters of said type may advantageously be produced by means of evaporization processes already known per se. This production method is economically very advantageous and provides furthermore a product which is mechanically very robust.

The invention is not limited to welding but can of course also be used in other applications, in which radiation of intensity harmful to the eye may be present.

In all the filters according to the examples given above, the transmission region has a certain width around the emission wavelength of the light source. This is so because if the transmission region of a filter is made too narrow, it could be displaced away from the emission region of the light source because of the tolerances of the widths of the layers, which are always inherent in the manufacturing of the filter. Therefore, if the transmission region is made too narrow, the manufacturing tolerances have to be very limited, and accordingly could lead to a considerable number of rejections of manufactured filters.

For the filter embodiments according to the invention it is very difficult to make an unequivocal statement of the thickness tolerances involved for the separate layers, because the tolerances of the separate layers are mutually dependent.

In some situations, where the radiation from the arc is subject to extremely strong and sudden fluctuations, the transmission of the filters above would have to be quite low in order to allow for a sufficient safety margin against the risk of eye damage. In such cases the visibility through the filter even with the special light source may become too low for comfortable and efficient work.

Figure 17:
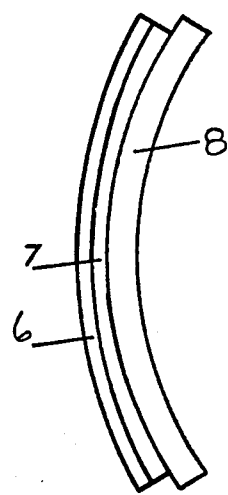
FIG. 17 illustrates a preferred design of the device when it is used as a protective device for welding.

An improvement in this respect can be achieved by the embodiment according to FIG. 17. In this embodiment the protective glass according to the invention comprises a combination of one of the above mentioned filter embodiments and a light sensitive substrate, the transmission of which is reduced upon increased illumination. In this manner the filter can be made more transmitting in its transmission band than what would be the case without the photochromic substrate. Thus, according to the invention, the welder can be given full visibility over his working area before the welding and in addition the eyes will be protected during the welding to radiation with a strongly fluctuating light intensity.

In FIG. 17, part 6 is a plane or curved plate of a photochemical substrate, for instance Compound 224 manufactured by Applied Photophysics Ltd. or comparative substances. Part 7 is the above described filter with multi-layer coating. Part 8 of the protective device consists of a plane or curved plate of, for instance, glass. The glass can be spectrally absorbing or transparent. As an example of an embodiment, color glass of type OG 560 manufactured by Jenaer Glaswerk, Schott & Genossen in Mainz could be used.

By means of the photochromic substrate 6 extra attenuation can be added at the intensity peaks of the fluctuating arc. The transmission of part 7 can therefore be permitted to be greater than without substrate 6, the risk for eye damage still being small, since the substrate and the filter are matched to each other in a manner which permits the protective device on welding to transmit only a light intensity which is harmless to the eye. A certain disturbing glare from the arc can arise on increased transmission. This effect, however, is not harmful since it is mainly of a psychological nature. The increased transmission is of great importance since it permits higher visibility through the protective device, for instance upon movements and transportations.

In FIG. 17, according to another embodiment part 8 of the protective glass can be comprised of Compound 224 or comparable whereas the plate 6 can be comprised either by a plane or curved plate of absorbing or non-absorbing glass or Compound 224 or comparable. Depending on whether the sensitivity of the photochromic material is low or high, it should be placed on the side of the interference filter which is nearer or further away from the welding arc, respectively.

The protective device of the invention need not comprise only a filter with the properties as described in the foregoing, but it may also comprise a combination of several filter units so as to allow an increase in the attenuation of the intensity of the transmitted light.

Thus, by giving the filter a structure as described in the foregoing, a filter has been obtained which transmits light only within the range or ranges of wavelengths of the light source, which attenuates the intensity of this light to a value which is harmless to the eye and which does not cause disturbing reflections to the surroundings. Filters of this type can be produced advantageously by evaporation processes of a known type. For example, layers 2, 3 and 4 may be applied to a plate of glass 1 by successive evaporation processes performed under a vacuum. The media 5 may be a plate of glass joined to the other portion of the filter, for example, by use of an optical cement with the same refractive index as the glass. However, it will be understood that the media 5 may comprise the surrounding air. This method of production is economically advantageous and gives moreover a mechanically very robust product.

The invention is not limited to welding but can also be used in different context, where radiation of an intensity which is harmful to the eye occurs, for example, during the firing of a rocket.

What is claimed is:

1. A protective device for protection against radiation, wherein a light source of emission mainly about a certain wavelength $\lambda$, is present in the surrounding region, said protective device including an interference filter comprising:
   a spectrally selective portion having a pass band for mainly the wavelength $\lambda$; and
   an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portions, and the non-absorbing material being selected from the group consisting of $SiO_2$ and $Al_2O_3$.

2. The protective device of claim 1 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

3. A protective device for protection against radiation, wherein a light source of emission mainly about a certain wavelength $\lambda$, is present in the surrounding region, said protective device including an interference filter comprising:
 a spectrally selective portion having a pass band for mainly the wavelength $\lambda$; and
 an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portions, and the non-absorbing material having a refractive index of 1.35.

4. The protective device of claim 3 wherein the non-absorbing material is selected from the group consisting of $MgF_2$ and $Na_3AlF_6$.

5. The protective device of claim 3 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

6. A protective device for protection against radiation, wherein a light source of emission mainly about a certain wavelength $\lambda$, is present in the surrounding region, said protective device including an interference filter comprising:
 a spectrally selective portion having a pass band for mainly the wavelength $\lambda$; and
 an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portions, and each absorbing portion consisting of
 a $SiO_2$ layers each with a thickness essentially 270 $(\lambda/589) \cdot (n_1(589)/n_1(\lambda))$ nanometers, and
 a$-1$ Cr layers each with a thickness essentially 6 nm, each Cr layer being disposed between two $SiO_2$ layers, wherein $n_1$ (589) is the refractive index of $SiO_2$ at the wavelength 589 nm and $n_1$ ($\lambda$) is the refractive index of $SiO_2$ at the wavelength $\lambda$, and in which $2 \leq a \leq 6$.

7. The protective device of claim 6 wherein $a=4$.

8. The protective device of claim 6, wherein the spectrally selective portion consists of two Ag-layers of a thickness of essentially 50 nm and an intermediate $MgF_2$-layer of a thickness of essentially 850 ($\lambda/589$) $(n_2(589)/n_2(\lambda))$ nanometers, wherein $n_2(589)$ is the refractive index of $MgF_2$ at the wavelength 589 nm and $n_2$ ($\lambda$) is the refractive index of $MgF_2$ at the wavelength $\lambda$.

9. The protective device of claim 6, wherein the spectrally selective portion consists of an essentially 33 nm thick Ag-layer, an essentially 306 ($\lambda/589$) $(n_3(589)/n_3(\lambda))$ nm thick $Al_2O_3$-layer, an essentially 77 nm thick Ag-layer, an essentially 841 ($\lambda/589$) $(n_3(589)/n_3(\lambda))$ nm thick $Al_2O_3$-layer and an essentially 33 nm thick Ag-layer.

10. The protective device of claim 6, wherein the spectrally selective portion consists of an essentially 33 nm thick Ag-layer, an essentially 385 $(\lambda/589)(1.35/n_4(\lambda))$ nm thick layer of a material with refractive index $n=1.35$ at the wavelength $\lambda=589$ nm, an essentially 77 nm thick Ag-layer, an essentially 604 ($\lambda/589$) $(1.35/n_4(\lambda))$ nm thick layer of said material and an essentially 33 nm thick Ag-layer, where $n_4$ ($\lambda$) is the refractive index of said material at the wavelength $\lambda$.

11. The protective device of claim 6 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

12. A protective device for protection against radiation, wherein a light source of emission mainly about a certain wavelength $\lambda$, is present in the surrounding region, said protective device including an interference filter comprising:
 a spectrally selective portion having a pass band for mainly the wavelength $\lambda$; and
 an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portion, and each absorbing portion consisting of two outer $Al_2O_3$ layers of a thickness essentially 227 ($\lambda/589$)/$n_3(589)/n_3(\lambda))$ nm and inside of each outer $Al_2O_3$ layer a Cr-layer of a thickness of essentially 6 nm, and inside each of said Cr-layers an $Al_2O_3$-layer of a thickness of essentially 76 ($\lambda/589$)$(n_3(589)/n_3(\lambda))$ nm, and
 a central layer of Cr of the thickness of essentially 14 nm.

13. The protective device of claim 12, wherein the spectrally selective portion consists of an essentially 33 nm thick Ag-layer, an essentially 306 ($\lambda/589$) $(n_3(589)/n_3$ ($\lambda$)) nm thick $Al_2O_3$-layer, an essentially 77 nm thick Ag-layer, an essentially 841 ($\lambda/589$)

$(n_3(589)/n_3(\lambda))$ nm thick $Al_2O_3$-layer and an essentially 33 nm thick Ag-layer.

14. The protective device of claim 12, wherein the spectrally selective portion consists of an essentially 33 nm thick Ag-layer, an essentially 385 $(\lambda/589)$ $(1.35/n_4(\lambda))$ nm thick layer of a material with refractive index $n=1.35$ at the wavelength $\lambda=589$ nm, an essentially 77 nm thick Ag-layer, an essentially 604 $(\lambda/589)(1.35/n_4(\lambda))$ nm thick layer of said material and an essentially 33 nm thick Ag-layer, where $n_4(\lambda)$ is the refractive index of said material at the wavelength $\lambda$.

15. The protective device of claim 12 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

16. A protective device for protection against radiation, wherein a light source of emission mainly about a certain wavelength $\lambda$, is present in the surrounding region, said protective device including an interference filter comprising:

a spectrally selective portion having a pass band for mainly the wavelength $\lambda$; and an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portions, and each absorbing portion consisting of a layer of a material with the refractive index $n=1.35$ at the wavelength 589 nm of a thickness essentially 277 $(\lambda/589)(1.35/n_4(\lambda))$ nm, a Cr-layer of a thickness of essentially 7 nm, two layers of said material with a thickness of essentially 93 $(\lambda/589)(1.35/n_4(\lambda))$ and a Cr-layer between the last mentioned layers with a thickness of essentially 15 nm, where $n_4(\lambda)$ is the refractive index for said material at the wavelength $\lambda$.

17. The protective device of claim 6, wherein the spectrally selective portion consists of an essentially 33 nm thick Ag-layer, an essentially 385 $(\lambda/589)(1.35/n_4(\lambda))$ nm thick layer of a material with refractive index $n=1.35$ at the wavelength $\lambda=589$ nm, an essentially 77 nm thick Ag-layer, an essentially 604 $(\lambda/589)(1.35/n_4(\lambda))$ nm thick layer of said material and an essentially 33 nm thick Ag-layer, where $n_4(\lambda)$ is the refractive index of said material at the wavelength $\lambda$.

18. The protective device of claim 16 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

19. A protective device for protection against radiation, wherein a light source of emission mainly about a certain wavelength $\lambda$, is present in the surrounding region, said protective device including an interference filter comprising:

a spectrally selective portion having a pass band for mainly the wavelength $\lambda$; and an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portions, and each absorbing portion consisting of two outer $Al_2O_3$ layers of a thickness essentially 227 $(\lambda/589)/(n_3(589)/n_3(\lambda))$ nm and inside of each outer $Al_2O_3$ layer a Cr-layer of a thickness of essentially 6 nm, and inside each of said Cr-layers an $Al_2O_3$-layer of a thickness of essentially $76(\lambda/589)(n_3(589)/n_3(\lambda))$ nm, and a central layer consisting of two Cr-layers of the thickness of essentially 7 nm with an intermediate $Al_2O_3$-layer of essentially $76(\lambda/589)(n_3(589))/n_3(\lambda)$, where $n_3(589)$ is the refractive index of $Al_2O_3$ at the wavelength 589 nm and $n_3(\lambda)$ is the refractive index of $Al_2O_3$ at the wavelength $\lambda$.

20. The protective device of claim 19, wherein the spectrally selective portion consists of an essentially 33 nm thick Ag-layer, an essentially 306 $(\lambda/589)(n_3(589)/n_3(\lambda))$ nm thick $Al_2O_3$-layer, an essentially 77 thick Ag-layer, an essentially 841 $(\lambda/589)(n_3(589)/n_3(\lambda))$ nm thick $Al_2O_3$-layer and an essentially 33 nm thick Ag-layer.

21. The protective device of claim 19, wherein the spectrally selective portion consists of an essentially 33 nm thick Ag-layer, an essentially 385 $(\lambda/589)(1.35/n_4(\lambda))$ nm thick layer of a material with refractive index $n=1.35$ at the wavelength $\lambda=589$ nm, an essentially 77 nm thick Ag-layer, an essentially 604 $(\lambda/589)$ $(1.35/n_4(\lambda))$ nm thick layer of said material and an essentially 33 nm thick Ag-layer, where $n_4(\lambda)$ is the refractive index of said material at the wavelength $\lambda$.

22. The protective device of claim 19 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

23. A protective device for protection against radiation, wherein a light source of emission mainly about a certain wavelength $\lambda$, is present in the surrounding region, said protective device including an interference filter comprising:

a spectrally selective portion having a pass band for mainly the wavelength $\lambda$; and an absorbing portion on each side of said spectrally selective portion, said absorbing portion being adapted to hold the reflectance at least over the entire visible spectrum in the boundary surface between the interference filter and the surrounding region at a level below 15%, each of the absorbing portions including alternating layers of chromium and a non-absorbing material, the non-absorbing material layers being the outermost layers of said absorbing portions, and the non-absorbing material having an index of refraction less than or equal to 1.46 and wherein said spectrally selective portion includes alternating layers of a metallic material and a dielectric material arranged with respect to the layers of said absorbing portion such that the adjacent layers of said absorbing portions and said spectrally selective portion are not both of a metallic material.

24. The protective device of claim 23 further including a layer of light sensitive material disposed on one of the outer surfaces of the absorbing part of said interference filter, the layer of light sensitive material in said interference filter cooperating to provide decreasing transmission of light passing therethrough at increasing intensity of illumination of such light, so that only light of an intensity harmless to the eye will pass through said protective device.

* * * * *